(12) United States Patent
Christensen

(10) Patent No.: US 6,702,858 B2
(45) Date of Patent: Mar. 9, 2004

(54) LINER FOR PROSTHETIC SOCKET WITH VARIABLE VISCOSITY FLUID

(75) Inventor: Roland J. Christensen, 192 E. 100 North, Fayette, UT (US) 84630

(73) Assignee: Roland J. Christensen, Fayette, UT (US)

(*) Notice: Subject to any disclaimer, the term of this patent is extended or adjusted under 35 U.S.C. 154(b) by 0 days.

(21) Appl. No.: 10/147,331

(22) Filed: May 15, 2002

(65) Prior Publication Data
US 2003/0216815 A1 Nov. 20, 2003

(51) Int. Cl.⁷ .................................................. A61F 2/80
(52) U.S. Cl. ........................................ 623/37; 623/37
(58) Field of Search ..................................... 623/33–37

(56) References Cited

U.S. PATENT DOCUMENTS

| | | | |
|---|---|---|---|
| 3,548,420 A | * | 3/1967 | Spence .............................. 3/20 |
| 3,663,973 A | * | 5/1972 | Spence .......................... 5/348 |
| 3,858,379 A | * | 1/1975 | Graves et al. .................. 53/25 |
| 5,108,456 A | * | 4/1992 | Coonan, III .................. 623/37 |
| 5,458,656 A | | 10/1995 | Phillips |
| 5,571,183 A | * | 11/1996 | Kazem et al. ................. 623/11 |
| 5,571,210 A | | 11/1996 | Lindh |
| 5,571,213 A | | 11/1996 | Allen |
| 5,779,735 A | | 7/1998 | Molino |
| 5,800,565 A | | 9/1998 | Biedermann |
| 5,893,891 A | | 4/1999 | Zahedi |
| 6,019,795 A | | 2/2000 | Phillips |
| 6,197,068 B1 | | 3/2001 | Christensen |
| 6,280,479 B1 | | 8/2001 | Phillips |
| 6,423,098 B1 | * | 7/2002 | Biedermann .................. 623/24 |
| 6,443,993 B1 | * | 9/2002 | Koniuk .......................... 623/24 |

FOREIGN PATENT DOCUMENTS

GB 1191633 5/1970

* cited by examiner

*Primary Examiner*—Bruce Edward Snow
(74) *Attorney, Agent, or Firm*—Thorpe North & Western

(57) ABSTRACT

A socket device of a prosthetic includes a liner with a variable viscosity fluid disposed between the socket and the user's stump. The variably viscosity fluid varies the softness or stiffness of socket. In addition, the variable viscosity fluid conforms to the contours of the user's stump for a more customized fit. The variable viscosity fluid can include a shear stiffening material that increases in viscosity as a load or strain, or rate of loading or rate of strain, applied, or a magneto or electro rheologic fluid responsive to a magnetic or electric field.

26 Claims, 4 Drawing Sheets

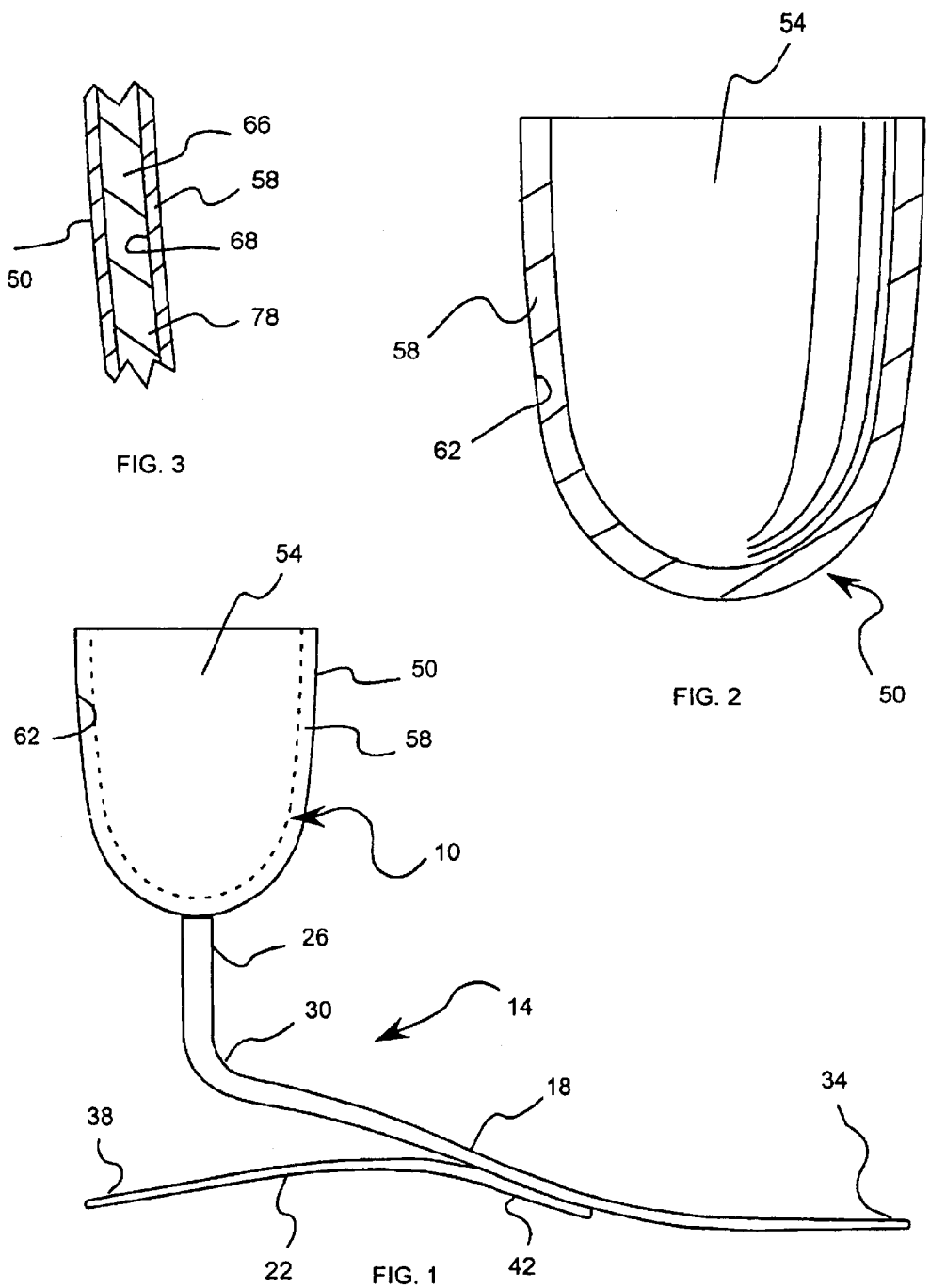

LINER FOR PROSTHETIC SOCKET WITH VARIABLE VISCOSITY FLUID

BACKGROUND OF THE INVENTION

1. Field of the Invention

The present invention relates generally to prosthetics. More particularly, the present invention relates to a socket of a prosthetic for receiving the stump of an amputee, and which includes a variable viscosity fluid.

2. Related Art

Many individuals have lost a limb for various reasons including war, accident, or disease. In most instances, these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward. Examples of such energy storing, spring-like feet include U.S. Pat. Nos. 5,037,444; 4,547,913; 5,181,932 and 5,976,191. The prosthetic feet typically include spring-like members that are typically flexible and resilient. In order to provide a natural feel and cushion of a natural foot, the members must be flexible and deflect under the user's weight.

Such prosthetic feet typically include a socket for receiving the user's stump. The prosthetic foot or spring can be attached to the socket, attached to pylon that is attached to the socket, or the like. It is desirable to provide a socket that is comfortable for transferring forces from the prosthetic, such as the prosthetic foot, to the user's stump. In addition, is it desirable to provide a socket that accommodates the swelling and/or contracting of the user's stump.

SUMMARY OF THE INVENTION

It has been recognized that it would be advantageous to develop a prosthetic or socket thereof that is comfortable, or that provides a comfortable fit with the user's stump, and which is comfortable during use. In addition, it has been recognized that it would be advantageous to develop a prosthetic or socket thereof that accommodates the swelling and/or contraction of a user's stump.

The invention provides a socket device to attach a prosthetic to a stump of an amputee. The socket device can include an outer shell coupled to the prosthetic and has a cavity to receive the stump of the amputee. An internal liner is disposed in the cavity of the outer shell, and is disposed between the stump of the amputee and an internal surface of the cavity. The internal liner advantageously includes a variable viscosity fluid to variably transfer energy between the stump of the amputee and the outer shell in response to changes in load applied to the liner. In addition, the variable viscosity fluid of the internal liner can accommodate the swelling and/or contracting of the user's stump.

In accordance with a more detailed aspect of the present invention, the internal liner can include a bladder having a hollow with the variable viscosity fluid disposed therein. In addition the internal liner can further include a layer of cushion material.

In accordance with another more detailed aspect of the present invention, the variable viscosity fluid can include a shear stiffening material that increases in viscosity with an increase in a load factor applied to the shear stiffening material. The load factor can include a load, a load rate, a strain, or a strain rate.

In accordance with another more detailed aspect of the present invention, the variable viscosity fluid can include a magneto rheologic fluid responsive to a magnetic field. In addition, the variable viscosity fluid can include an electro rheologic fluid responsive to an electric field.

In accordance with a more detailed aspect of the present invention, a transducer can be coupled to the prosthetic or socket to sense strain. A power source can be coupled to the transducer. Control electronics can be coupled to the transducer and the variable viscosity fluid to apply the electric field in response to the strain sensed by the transducer.

In accordance with another more detailed aspect of the present invention, an orifice can be provided through which the variable viscosity fluid flows, or is forced, during use.

In accordance with another more detailed aspect of the present invention, the internal liner and variable viscosity fluid can be flexible and conform to fit the contours of the stump of the user.

In accordance with another more detailed aspect of the present invention, the internal liner can further include a plurality of flexible compartments, at least one of the compartments containing the variable viscosity fluid.

A method for varying a stiffness of a socket of a prosthetic and conforming the socket to a stump of an amputee includes inserting the stump of an amputee into a socket of a prosthetic. The socket includes a shell shaped and sized to receive the stump, and a variable viscosity fluid disposed between the shell and the stump of the amputee. The shape of the liner and the variable viscosity fluid are changed to match contours of the stump of the amputee. The viscosity of the fluid is varied in response to loading on the shell or the prosthetic foot, so that the stiffness of the variable viscosity fluid varies, including increasing viscosity during increased loading for a stiffer feel during the increased loading, and decreasing viscosity during decreased loading for a softer feel during the decreased loading. In addition, the shape of the liner and the viscosity of the fluid can accommodate the swelling and/or contraction of the user's stump.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 1 is a side view of a prosthetic foot having a socket with a variable viscosity fluid in accordance with an embodiment of the present invention;

FIG. 2 is a cross-sectional side view of the socket of FIG. 1;

FIG. 3 is a partial, cross-sectional view of the socket of FIG. 1;

DETAILED DESCRIPTION

Figure 4:
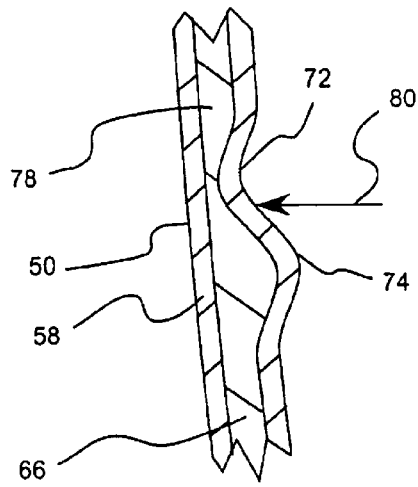
FIGS. 4 and 5 are cross-sectional schematic views of a socket with a variable viscosity fluid including a shear stiffening material in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in the figures, various embodiments of sockets for prosthetics in accordance with the present invention are shown that advantageously include a variable viscosity fluid or material. The variable viscosity fluid or material is located in the socket between the socket and the user's stump. The variable viscosity of the fluid or material advantageously allows the fluid to conform to the contours of the user's stump, and/or to vary the cushion or stiffness of the fluid. As described in greater detail below, the variable viscosity fluid or material can include a shear stiffening material that increases in viscosity as load or strain, or load rate or strain rate, is applied; an electro rheologic fluid that changes viscosity under an applied electric field; or a magneto rheologic fluid that changes viscosity under an applied magnetic field. While the invention is shown and described by way of example with respect to a prosthetic foot, it is of course understood that the invention can be used with other prosthetics.

As illustrated in FIGS. 1–3, a socket device, indicated generally at 10, in accordance with the present invention is shown for attaching a prosthetic foot 14 to a stump of an amputee. The socket device 10 can be attached to the prosthetic foot 14 in various ways, as is well known in the art. The prosthetic foot 14 can have various different configurations, also as is well known in the art. The configuration of the prosthetic foot 14 shown in the figures is by way of example. It is of course understood that the prosthetic foot 14 can have various different configurations. As an example, the prosthetic foot 14 can include a first or upper member 18 that can be sized and shaped as a forefoot or upper foot member that extends from an attachment portion 26, which is coupled to the socket 10, downwardly through an arcuate portion 30, to a toe section 34. In addition, the prosthetic foot 14 can include a second or lower member 22 that can be sized and shaped as a heel member that extends from a heel portion 38 to a coupling section 42 coupled to the first member 18. The heel portion 38 of the second member 22 can be located at a heel location in a region near the rear of the foot 14 where the heel of a natural foot would be located. Similarly, the toe portion 34 is located at a toe location in a region near the front of the foot 14 where the toes of a natural foot would be located.

The socket 10 is configured for the specific needs of the amputee, but includes a portion adapted for standard attachment. The attachment portion 26 of the prosthetic foot 14 can be attached to the socket 10 by any means, as is known in the art. The first member 18 can be curved in a general L-shape or a J-shape, with the socket 10 attaching to the side or end of the attachment portion 26 forming a vertical attachment. Alternatively, a first member can be curved in a general C-shape, with the socket attaching to a top of the attachment portion 26 forming a horizontal attachment.

The first and second members 18 and 22 can be resilient and energy storing foot members that deflect or flex, storing energy, much like a leaf spring. Thus, the first and second members 18 and 22 can be formed of a flexible and resilient material that allows the foot members to deflect or flex. In one aspect, the members 18 and 22 can be formed of a fiber reinforced resin material, such as a graphite-reinforced resin.

The socket 10 includes an outer shell 50 with a cavity 54 to receive the user's stump. The shell 50 can be formed of a molded plastic, and can be rigid to form a rigid connection with the foot 14. An internal liner 58 is disposed in the cavity 54, between the shell 50 and the user's stump. The liner 58 can be attached to an internal surfaced 62 of the cavity 54 of shell 50. The liner 58 can include a compliant material, such as foam or the like. The liner 58 can provide a cushioned, soft feel to the shell.

The internal liner 58 advantageously includes a variable viscosity fluid or material 66. The variable viscosity fluid 66 can be included in pockets or cavities formed within the liner 58, or the variable viscosity fluid 66 can form substantially the entire liner. The variable viscosity fluid or material 66 can be disposed or contained in flexible bags or bladders 68. The bladder 68 can be disposed in the internal liner 58, or can be formed by the liner 58. Alternatively, the bladder can be attached to the inner surface 62 of the shell 50.

Figure 5:
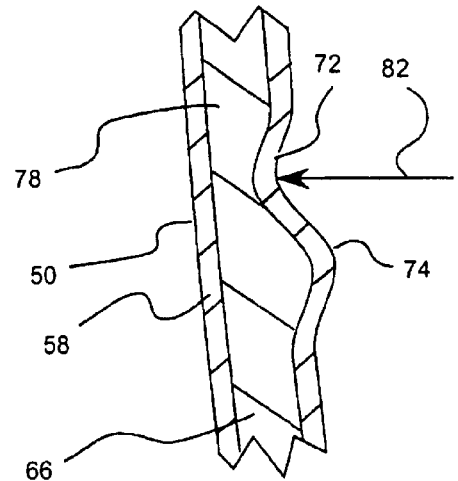

Referring to FIGS. 4 and 5, the variable viscosity fluid or material 66 can displace to contour to the user's stump. For example, the variable viscosity fluid or material 66 can allow the liner 58 to form indentations 72 and/or protrusions 74 to match the user's stump, thus creating a more comfortable, custom fit. In addition, the variable viscosity fluid 66 displaces so that fluid adjacent the indentations 72 displaces away from the indentations 72, and can displace into the protrusions 74. Thus, the displacement of the fluid 66 allows the liner 58 to provide a more uniform pressure over the surface of the user's stump, unlike a typical foam that compresses, resulting in areas of greater pressure. In addition, the fluid 66 and liner 58 can accommodate swelling and/or contraction of the user's stump.

As stated above, the variable viscosity fluid or material 66 can include a shear stiffening material 78. Such a shear stiffening material 78 increases in viscosity in response to a load factor, or as a load factor increases. Such a load factor can include a load, a load rate, a strain or a strain rate. An example of such shear stiffening material is a composition of cornstarch and water. Under little or no load or strain (indicated by arrow 80), the shear stiffening material 78 can be less viscous and capable of greater flow, and thus the liner 58 can be more compressible, as shown in FIG. 4. Under greater load or strain (indicated by arrow 82), the shear stiffening material 78 can be more viscous and less capable of flowing, and thus the liner 58 can be less compressible, as shown in FIG. 5. It will be appreciated that the less-viscous shear stiffening material dissipates more energy or force so that the shell 50 or liner 58 has a softer feel. The more-viscous shear stiffening material, however, provides a stiffer feel, and a tighter fit.

Figure 6:
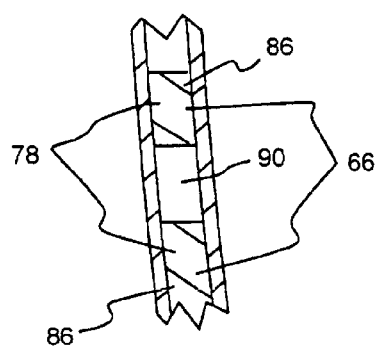
FIGS. 6 and 7 are partial, cross-sectional views of another socket with a variable viscosity fluid in accordance with an embodiment of the present invention.
Figure 7:
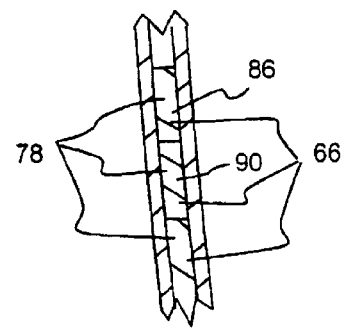

Referring to FIGS. 6 and 7, the variable viscosity fluid or material 66, or the shear stiffening material 78, can be disposed in pockets 86 formed in the liner 58. Cavities or empty pockets 90 also can be disposed in the liner 58, as shown in FIG. 6. During loading, the variable viscosity fluid 66 or the shear stiffening material 78 can be displaced from the pockets 86 and into the cavities 90, as shown in 7. After the loading is removed, the variable viscosity fluid 66 or the shear stiffening material 78 can return to the pockets 86.

Figure 9:
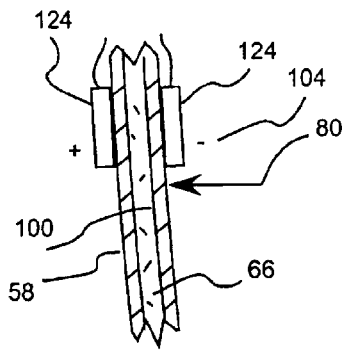
FIGS. 9 and 10 are partial, cross-sectional schematic views of another socket with a variable viscosity fluid including an electro rheologic material in accordance with an embodiment of the present invention.
Figure 10:
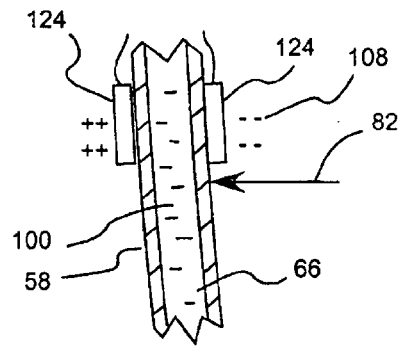
Figure 8:
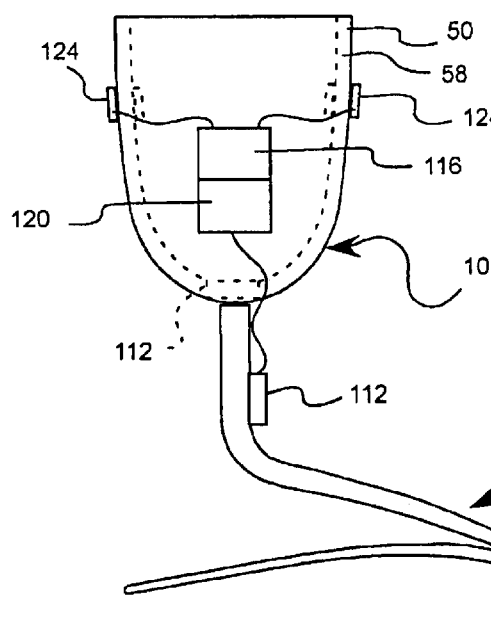
FIG. 8 is a side view of another prosthetic foot having a socket with a variable viscosity fluid in accordance with an embodiment of the present invention.

Referring to FIGS. 8–10, the variable viscosity fluid or material 66 can include an electro rheologic fluid 100 that is responsive to an applied electric field to alter its viscosity. Such an electro rheologic fluid 100 increases in viscosity as an electric field is applied. Under little or no electric field (indicated at 104), the electro rheologic fluid 100 can be less viscous and capable of greater flow, and thus the liner 58 can be more compressible, as shown in FIG. 9. Under a greater electric field (indicated at 108), the electro rheologic fluid 100 can be more viscous and less capable of flowing, and thus the liner 58 can be less compressible, as shown in FIG. 10. Again, it will be appreciated that the less-viscous electro rheologic fluid dissipates more energy or force so that the liner 58 and shell 50 are softer. The more-viscous electro rheologic material, however, provides a stiffer feel, and a tighter fit.

Referring again to FIG. 8, the prosthetic foot 14 or socket 10 can include a transducer 112, such as a strain gauge, coupled to the member 18 and 22, and/or the shell 50 or bladder 54. The transducer 112 senses strain or deformation in the members 18 and 22, or shell 50. The transducer 112 can be operatively coupled to control electronics 116 and a power source 120. The control electronics 116 and the transducer 112 can be operatively coupled to the electro rheologic fluid, such as by electrodes 124. The control electronics 116 can include amplifier circuitry, while the power source 120 can be a battery. The transducer 112 senses deflection or strain in the members 18 and 22 or shell 50 and produces a signal that can be sent to the control electronics 116. The control electronics 116 can include amplifier circuitry to amplify the signal to create a control signal. In addition, the control electronics 116 can include circuitry to accept only signals that correspond to a predetermined minimum strain or deflection. The control signal can be applied to the electro rheologic fluid 100 by the electrodes 124. It will be appreciated that the control electronics 116 can include inputs to vary the amplification, minimums, etc., to control or customize the feel of the socket.

Referring to FIGS. 9 and 10, such an electro rheologic fluid 100 can include particles or filings in an oil. As the electric field 108 is applied, the particles or filings align, increasing the viscosity of the fluid 100, or the oil with particles or filings. With no or little electrical field 104, the particles or filings are random, decreasing the viscosity of the fluid 100, or the oil with particles or filings.

Figure 11:
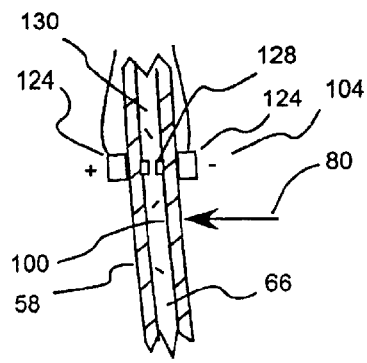
FIG. 11 is a partial, cross-sectional schematic view of another socket with a variable viscosity fluid including an electro rheologic material in accordance with an embodiment of the present invention.

Referring to FIG. 11, an orifice 128 can be provided through which the electro rheologic fluid 100 flows during use. Under little or no electric field 104, the electro rheologic fluid 100 is less viscous, and more easily flows through the orifice 128, to allow the fluid 100 to be displaced. Under a greater electric field (108 in FIG. 10), the electro rheologic fluid 100 is more viscous, and flows through the orifice 128 less easily, or not at all, to resist the fluid 100 from displacing. The electro rheologic fluid 100 can be forced through, or can pass through, the orifice 128 and into a reservoir 130 under loading of the socket or foot. The electrodes 124 can be disposed around the orifice 128 to apply and electric field at or near the orifice. The electro rheologic fluid 100 is responsive to the applied electric field to alter its viscosity. Such an electro rheologic fluid 100 increases in viscosity as the electric field is applied, thus impeding the flow of the fluid 100 through the orifice 128. Under little or no electric field (indicated at 104), the electro rheologic fluid 100 can be less viscous and capable of greater flow, and thus can pass through the orifice 128, as shown in FIG. 11. Therefore, under lesser force or load 80, the fluid 100 flows through the orifice 128 for a softer feel. Under a greater electric field (similar to 108 in FIG. 10), the electro rheologic fluid 100 can be more viscous and less capable of flowing, and thus is impeded from flowing through the orifice 128. Therefore, under greater force or load (similar to 82 in FIG. 10), the fluid provides a stiffer feel, and a tighter fit.

Figure 12:
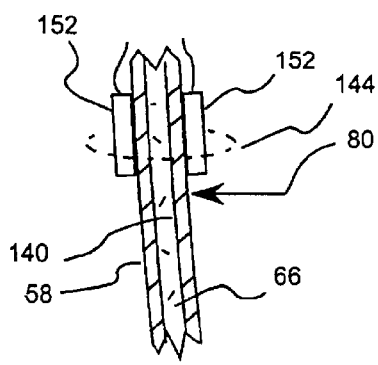
FIGS. 12 and 13 are partial, cross-sectional schematic views of another socket with a variable viscosity fluid including a magneto rheologic material in accordance with an embodiment of the present invention.
Figure 13:
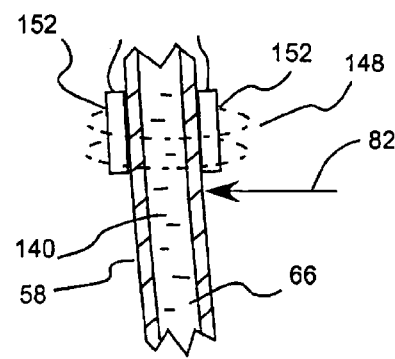

Referring to FIGS. 12 and 13, the variable viscosity fluid or material 66 can include a magneto rheologic fluid 140 that is responsive to an applied magnetic field to alter its viscosity. Such a magneto rheologic fluid 140 increases in viscosity as a magnetic field is applied. Under little or no magnetic field (represented by lines 144), the magneto rheologic fluid 140 can be less viscous and capable of greater flow, and thus the liner 58 can be compressible, as shown in FIG. 12. Under a greater magnetic field (represented by lines 148), the magneto rheologic fluid 140 can be more viscous and less capable of flowing, and thus the liner 58 can be less compressible, as shown in FIG. 13. Again, it will be appreciated that the less-viscous magneto rheologic fluid dissipates more energy or force so that the liner is softer. The more-viscous magneto rheologic material, however, provides a stiffer feel, and a tighter fit.

The magnetic field can be applied by magnets 152 that are operatively coupled to the fluid 140 or shell 50. The magnets 152 can be electromagnets operatively coupled to the control electronics 116 (FIG. 8) using the control signal to generate the magnetic field. Such a magneto rheologic fluid 140 can include particles or filings in an oil. As the magnetic field 148 is applied, the particles or filings align, increasing the viscosity of the fluid, or the oil with particles or filings. With little or no magnetic field 144, the particles or filings are random, decreasing the viscosity of the fluid, or the oil with particles or filings.

Figure 14:
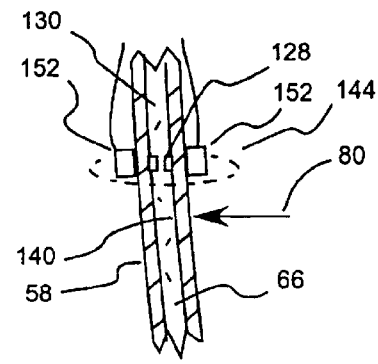
FIG. 14 is a partial, cross-sectional schematic view of another socket with a variable viscosity fluid including a magneto rheologic material in accordance with an embodiment of the present invention.

Referring to FIG. 14, an orifice 128 can be provided through which the magneto rheologic fluid 140 flows during use. Under little or no magnetic field 144, the magneto rheologic fluid 140 is less viscous, and more easily flows through the orifice 128, to allow the fluid 140 to be displaced. Under a greater magnetic field (148 in FIG. 13), the magneto rheologic fluid 140 is more viscous, and flows through the orifice 128 less easily, or not at all, to resist the fluid 140 from displacing. The magneto rheologic fluid 140 can be forced through, or can pass through, the orifice 128 and into a reservoir 130 under loading of the socket or foot. The magnets 148 can be disposed around the orifice 128 to apply a magnetic field at or near the orifice 128. The magneto rheologic fluid 140 is responsive to the applied magnetic field to alter its viscosity. Such a magneto rheologic fluid 140 increases in viscosity as the magnetic field is applied, thus impeding the flow of the fluid 140 through the orifice. Under little or no magnetic field (indicated at 144), the magneto rheologic fluid 140 can be less viscous and capable of greater flow, and thus can pass through the orifice 128, as shown in FIG. 14. Therefore, under lesser force or load 80, the fluid 140 flows through the orifice 128 for a softer feel. Under a greater magnetic field (similar to 82 in FIG. 13), the magneto rheologic fluid 140 can be more viscous and less capable of flowing, and thus is impeded from flowing through the orifice 128. Therefore, under greater force or load (82 in FIG. 13), the fluid provides a stiffer feel, and a tighter fit.

The operation of the socket 50 is described above, with a lower force application, such as walking, illustrated in FIGS. 4, 9 and 12, and with a higher force application, such as running, illustrated in FIGS. 5, 10 and 13. Referring to FIGS. 4, 9 and 12, as the user steps, an applied force, such as the user's weight, is applied to the liner 58 and shell 50. The user applies a force to the variable viscosity fluid 66 that may be a lesser force 80 due to the operation of the foot in a walking application. The variable viscosity fluid 66 displaces or compress to a greater extent, dissipating some of the force, and transferring less force to the user's stump. Thus, the variable viscosity fluid 66 provides a soft, cushioned feel.

Referring to FIGS. 5, 10 and 13, as the user exerts a greater force, such as by running, a greater force 82 is applied to the liner 58 and shell 50. The variable viscosity fluid 66 dissipates less or no force, and transfers more or all of the force to the user's stump for a stiffer feel and tighter fit. As described above, the variable viscosity fluid 66 can be a shear stiffening material 78 (FIGS. 4 and 5) that increases viscosity due to the applied load or strain. Or the variable viscosity fluid 66 can be a magneto or electro rheologic fluid 100 or 140 (FIGS. 9 and 10, or 12 and 13) that increases viscosity due to the application of a magnetic or electric field corresponding to the strain or deflection sensed by the transducer.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A socket device configured to attach a prosthetic to a stump of an amputee, the device comprising:
    a) an outer shell, configured to be coupled to the prosthetic, having an internal surface and a cavity configured to receive the stump of the amputee; and
    b) an internal liner, disposed in the cavity of the outer shell, configured to be disposed between the stump of the amputee and the internal surface of the cavity;
    c) the internal liner including a variable viscosity fluid to vary viscosity and stiffness during use, the variable viscosity fluid being capable of increasing viscosity during increased loading or rate of loading to transfer more load between the outer shell and the stump of the user during the increased loading or rate of loading, and being capable of decreasing viscosity during decreased loading or rate of loading to transfer less load between the outer shell and the stump of the user during the decreased loading or rate of loading.

2. A device in accordance with claim 1, wherein the variable viscosity fluid includes a shear stiffening material that increases with an increase in a load factor applied to the shear stiffening material.

3. A device in accordance with claim 2, wherein the load factor includes at least one load factor selected from the group consisting of: a load, a load rate, a strain, or a strain rate.

4. A device in accordance with claim 1, wherein the variable viscosity fluid includes at least one fluid selected from the group consisting of: a magneto rheologic fluid responsive to a magnetic field, or an electro rheologic fluid responsive to an electric field.

5. A device in accordance with claim 4, further comprising:
    a transducer to sense strain;
    a power source, coupled to the transducer;
    control electronics, coupled to the transducer and the variable viscosity fluid, to apply the electric field in response to the strain sensed by the transducer.

6. A device in accordance with claim 1, wherein the internal liner includes a bladder having a hollow with the variable viscosity fluid disposed therein.

7. A device in accordance with claim 1, wherein the internal liner further includes a layer of cushion material.

8. A device in accordance with claim 1, further comprising:
    an orifice through which the variable viscosity fluid flows during use.

9. A device in accordance with claim 1, wherein the internal liner and variable viscosity fluid are flexible and conform to fit the contours of the stump of the user.

10. A device in accordance with claim 1, wherein the internal liner further includes:
    a plurality of flexible compartments; and
    at least one of the compartments containing the variable viscosity fluid.

11. A method for varying a stiffness of a socket of a prosthetic and conforming the socket to a stump of an amputee, comprising the steps of:
    a) inserting the stump of an amputee into a socket of a prosthetic, the socket including i) a shell shaped and sized to receive the stump, and ii) a variable viscosity fluid disposed between the shell and the stump of the amputee;
    b) changing a shape of the liner and the variable viscosity fluid to match contours of the stump of the amputee; and
    c) varying the viscosity of the fluid in response to loading on the shell or the prosthetic foot, so that the stiffness of the variable viscosity fluid varies, including increasing viscosity during increased loading for a stiffer feel during the increased loading, and decreasing viscosity during decreased loading for a softer feel during the decreased loading; the variable viscosity fluid being selected from the group consisting of: a shear stiffening material that increases in viscosity with an increase in a load factor applied to the shear stiffening material; a magneto rheologic fluid responsive to a magnetic field; and an electro rheologic fluid responsive to an electric field.

12. A socket device configured to attach a prosthetic to a stump of an amputee, the device comprising:
   a) an outer shell, configured to be coupled to the prosthetic, having an internal surface and a cavity configured to receive the stump of the amputee; and
   b) an internal liner, disposed in the cavity of the outer shell, configured to be disposed between the stump of the amputee and the internal surface of the cavity;
   c) the internal liner including a variable viscosity fluid to variably transfer energy between the stump of the amputee and the outer shell in response to changes in load applied to the liner;
   d) the variable viscosity fluid being selected from a group consisting of:
      i) a shear stiffening material that increases in viscosity with an increase in a load factor applied to the shear stiffening material;
      ii) a magneto rheologic fluid responsive to a magnetic field; and
      iii) an electro rheologic fluid responsive to an electric field.

13. A device in accordance with claim 1, wherein the internal liner includes a bladder having a hollow with the variable viscosity fluid disposed therein.

14. A device in accordance with claim 1, wherein the internal liner further includes a layer of cushion material.

15. A device in accordance with claim 1, wherein the load factor includes at least one load factor selected from the group consisting of: a load, a load rate, a strain, or a strain rate.

16. A device in accordance with claim 1, further comprising:
   a transducer to sense strain;
   a power source, coupled to the transducer;
   control electronics, coupled to the transducer and the variable viscosity fluid, to apply the electric field in response to the strain sensed by the transducer.

17. A device in accordance with claim 1, further comprising:
   an orifice through which the variable viscosity fluid flows during use.

18. A device in accordance with claim 1, wherein the internal liner and variable viscosity fluid are flexible and conform to fit the contours of the stump of the user.

19. A device in accordance with claim 1, wherein the internal liner further includes:
   a plurality of flexible compartments; and
   at least one of the compartments containing the variable viscosity fluid.

20. A socket device configured to attach a prosthetic to a stump of an amputee, the device comprising:
   a) an outer shell, configured to be coupled to the prosthetic, having an internal surface and a cavity configured to receive the stump of the amputee; and
   b) an internal liner, disposed in the cavity of the outer shell, configured to be disposed between the stump of the amputee and the internal surface of the cavity;
   c) the internal liner including a variable viscosity fluid to variably transfer energy between the stump of the amputee and the outer shell in response to changes in load applied to the liner, the variable viscosity fluid includes at least one fluid selected from the group consisting of: a magneto rheologic fluid responsive to a magnetic field; and an electro rheologic fluid responsive to an electric field.

21. A device in accordance with claim 20, wherein the internal liner includes a bladder having a hollow with the variable viscosity fluid disposed therein.

22. A device in accordance with claim 20, wherein the internal liner further includes a layer of cushion material.

23. A device in accordance with claim 20, further comprising:
   a transducer to sense strain;
   a power source, coupled to the transducer;
   control electronics, coupled to the transducer and the variable viscosity fluid, to apply the electric field in response to the strain sensed by the transducer.

24. A device in accordance with claim 20, further comprising:
   an orifice through which the variable viscosity fluid flows during use.

25. A device in accordance with claim 20, wherein the internal liner and variable viscosity fluid are flexible and conform to fit the contours of the stump of the user.

26. A device in accordance with claim 20, wherein the internal liner further includes:
   a plurality of flexible compartments; and
   at least one of the compartments containing the variable viscosity fluid.

* * * * *